United States Patent [19]
Grey et al.

[11] Patent Number: 5,116,882
[45] Date of Patent: May 26, 1992

[54] PROCESS FOR MAKING COPOLYMERS OF VINYL AROMATIC MONOMERS AND VINYL PHOSPHONIC ACID DERIVATIVES AND FOAMED ARTICLES THEREFROM

[75] Inventors: Roger A. Grey, West Chester; Laurel E. Schock, Paoli; Diandre Armstead, Philadelphia, all of Pa.

[73] Assignee: Arco Chemical Technology, L.P., Wilmington, Del.

[21] Appl. No.: 701,279

[22] Filed: May 16, 1991

[51] Int. Cl.$^5$ .................. C08F 230/02; C08F 212/08; C08J 9/28

[52] U.S. Cl. ............................ 521/147; 252/609; 264/41; 264/51; 264/53; 264/54; 521/56; 521/60; 526/274; 526/275; 526/277; 526/278; 526/347

[58] Field of Search ............ 521/60, 56, 147; 526/278, 274, 275; 252/609

[56] References Cited

U.S. PATENT DOCUMENTS

| | | | |
|---|---|---|---|
| 2,439,214 | 4/1948 | Lindsey | 260/84 |
| 2,743,261 | 4/1956 | Coover, Jr. | 526/229 |
| 3,060,138 | 10/1962 | Wright | 521/60 |
| 3,063,954 | 11/1962 | Galizia | 521/60 |
| 3,726,839 | 4/1973 | Jin | 526/278 |
| 3,763,122 | 10/1973 | E'Fers | 526/278 |
| 3,967,999 | 7/1976 | Sommerfeld | 156/275.7 |
| 3,991,134 | 11/1976 | Kraft et al. | 260/859 R |
| 3,993,715 | 11/1976 | Hwa et al. | 260/884 |
| 4,035,571 | 7/1977 | Brunner et al. | 526/275 |
| 4,241,191 | 12/1980 | Keppler | 521/56 |
| 4,243,717 | 1/1981 | Gahmig | 428/402 |
| 4,444,969 | 4/1984 | Younes | 526/262 |

OTHER PUBLICATIONS

*Plast. Massy.* No. 8, (1966) 24.
*Plast. Massy*, No. 2 (166) 17.
*Chem. Abstracts* 72 32299g p. 4, Paragraph 1.
*Chem. Abstracts* 83 132379d p. 4, paragraph 1.
*Chem. Abstracts* 83 60019m p. 4, paragraph 1.
*Polym. Sci.*, USSR 24 (1982) 667 p. 4, paragraph 1.
*Macromolecules* 22 (1989) 4390 p. 4, paragraph 2.
*J. Organomet Al. Chem.* 12 (1968) 459 p. 4, paragraph 2.

*Primary Examiner*—Joseph L. Schofer
*Assistant Examiner*—Fred Zitomer
*Attorney, Agent, or Firm*—Jonathan L. Schuchardt

[57] ABSTRACT

A process for making thermoplastic copolymer beads from vinyl aromatic monomers and vinyl phosphonic acid derivatives is disclosed. A process for making foamed articles from the beads is also disclosed. The foamed articles are useful for packaging and construction applications.

30 Claims, No Drawings

PROCESS FOR MAKING COPOLYMERS OF VINYL AROMATIC MONOMERS AND VINYL PHOSPHONIC ACID DERIVATIVES AND FOAMED ARTICLES THEREFROM

FIELD OF THE INVENTION

The invention relates to copolymers of vinyl aromatic monomers and vinyl phosphonic acid derivatives. More specifically, the invention is a process for making copolymer beads by suspension polymerization and for making foamed articles from the beads.

BACKGROUND OF THE INVENTION

Expanded foams, particularly polystyrene foams, are widely used in the packaging and construction industries. Unfortunately, flame-retardant polystyrene with acceptable physical properties is difficult to manufacture. Halogenated flame-retardant additives used in flame-retardant polymers can leach out of the foam during burning and liberate harmful hydrogen halide vapors. In addition, many halogenated flame-retardant additives are unacceptable because they interfere with the polymerization, resulting in products that contain an undesirably high level of residual monomer. Chemical incorporation of flame retardants into the polymer backbone can give polymer products with good flame resistance and a reduced tendency to liberate harmful vapors. Unfortunately, ethylenically unsaturated monomers that incorporate flame-retardant moieties, particularly inexpensive, nonhalogenated ones, are in short supply.

Copolymers of vinyl phosphonic acid derivatives with olefinic compounds are known, and many variations are described in the patent literature. Thermoplastic, expandable beads of these copolymers useful for making foamed, flame-resistant articles have not been previously described.

U.S. Pat. No. 2,439,214 teaches copolymers of α, β-unsaturated phosphonic acids and diesters with monoethylenic compounds. The reference shows (Example IV) the bulk copolymerization of dimethyl 1-propene-2-phosphonate with styrene to produce a clear, colorless resin.

U.S. Pat. No. 2,743,261 teaches copolymers of α- and β-phosphonate styrenes (diesters) and monoethylenically unsaturated compounds. The copolymers are described as clear, tough, flame-resistant, hard resinous copolymers that can be molded into shaped objects or spun into fibers. The reference shows (Example I) bulk copolymerization of styrene and diethyl 1-phenyl vinyl phosphonate.

U.S. Pat. No. 3,726,839 teaches crosslinked polymers of a bis(hydrocarbyl) vinylphosphonate, a polyfunctional ethylenically unsaturated monomer such as divinylbenzene, and optionally a monofunctional vinyl comonomer. The compositions are useful as flame-retardant polymers or as polymer additives.

U.S. Pat. No. 3,763,122 teaches copolymers of styrene or acrylamide and phenyl vinyl phosphonic acids useful for improving the burst strength of paper.

U.S. Pat. No. 3,991,134 teaches copolymers of bis(hydrocarbyl) vinylphosphonates with halogen-containing $\alpha,\beta$-ethylenically unsaturated (vinyl) monomers. The reference teaches that mono(alkyl) acid vinylphosphonates can also be used.

U.S. Pat. No. 3,993,715 teaches a process for making fire-retardant polymers of bis(hydrocarbyl) vinyl phosphonates. A monoethylenically unsaturated monomer is added as a chaser to complete reaction of the phosphonate monomer.

U.S. Pat. No. 4,035,571 teaches copolymers of a bis(hydrocarbyl) vinylphosphonate, a monomer having one ethylenically unsaturated bond, and acrylic or methacrylic acid. The compositions are useful in coatings or as flame-retardant additives for thermoplastics. The reference teaches that these copolymers may be prepared by aqueous suspension polymerization. As shown in Example 2 of the reference, unreacted phosphonate monomer is recovered from the polymerization reaction mixture if the acrylic monomer is omitted.

U.S. Pat. No. 4,444,969 teaches copolymers of a vinyl-substituted aryl hydrocarbon monomer, an imide derivative of a cyclic anhydride, and a bis(hydrocarbyl) vinylphosphonate. The solid compositions are useful as fire-retardant additives.

A number of papers in the Russian literature describe the preparation of copolymers of α-phenylvinylphosphonic acid (PvPA) with vinyl monomers such as methyl methacrylate and styrene. Spherical granules useful as ion exchangers can reportedly be prepared by suspension polymerization if a crosslinking agent such as divinylbenzene is included (See, for example, *Plast. Massy*, No. 8 (1966) 24, *Plast. Massy*, No. 2 (1966) 17, *Chem. Abstr.* 72 32299g, *Chem. Abstr.* 83 132379d, and *Chem. Abstr.* 83 60019m). Such crosslinked copolymer beads are not expandable and therefore not suitable for use in the preparation of foamed articles. The radical copolymerization of dialkylvinyl phosphonates with styrene and methyl methacrylate was studied by Levin et al. (*Polym. Sci. USSR* 24 (1982) 667).

A recent paper (*Macromolecules* 22 (1989) 4390) describes a copolymer including a vinylphosphonic acid monoalkyl ester. Monoalkyl esters of this type have been prepared by basic hydrolysis of the corresponding diesters in dioxane (*J. Organometal. Chem.* 12 (1968) 459).

None of the references teaches a process wherein vinyl aromatic monomers and vinyl phosphonic acids are copolymerized in the absence of a crosslinking agent to give thermoplastic polymer beads. In addition, none of the above references teaches a process for the preparation of foamed articles from thermoplastic expandable copolymer beads made by suspension copolymerization of a vinyl aromatic monomer and a vinyl phosphonic acid derivative.

SUMMARY OF THE INVENTION

The invention is a process for making a foamed thermoplastic article. The process comprises molding foamed beads prepared by thermally expanding thermoplastic polymer beads. The thermoplastic polymer beads are made by copolymerizing in an aqueous suspension a vinyl aromatic monomer and a vinyl phosphonic acid or a vinyl phosphonate mono- or diester. The beads are impregnated with a foaming agent either during or following polymerization.

As will be shown, the success of the suspension copolymerization of the vinyl aromatic monomer and vinyl phosphonic acid derivative in forming satisfactory polymer beads depends on many factors, including which phosphonic acid derivative is involved.

The invention also relates to a process for making expandable thermoplastic beads. The beads are prepared by copolymerizing in an aqueous suspension: (a) a vinyl aromatic monomer, and (b) a vinyl phosphonic acid in the presence of partially hydrolyzed polyacrylamide and at least about 5 weight percent of an alkali metal halide or alkaline earth metal halide salt based on the amount of water used.

Another process of the invention comprises copolymerizing in an aqueous suspension: (a) a vinyl aromatic monomer, and (b) a vinyl phosphonic acid in the presence of partially hydrolyzed polyacrylamide and a tetraalkylammonium salt.

Another process of the invention comprises copolymerizing in an aqueous suspension: (a) a vinyl aromatic monomer, and (b) a vinyl phosphonate diester in the presence of a high-temperature radical initiator.

Another process of the invention comprises copolymerizing in an aqueous suspension: (a) a vinyl aromatic monomer, and (b) a vinyl phosphonate monoester in the presence of partially hydrolyzed polyacrylamide. The monoester can be conveniently generated in situ from the corresponding diester.

Another process of the invention comprises copolymerizing in an aqueous suspension a vinyl aromatic monomer and a vinyl phosphonic acid or a vinyl phosphonate mono- or diester in the presence of a foaming agent and a wax to produce expandable thermoplastic polymer beads.

DETAILED DESCRIPTION OF THE INVENTION

Suspension copolymerization of vinyl aromatic monomers and vinyl phosphonic acids is complicated by the fact that the phosphonic acids usually have greater solubility in water than in the vinyl aromatic monomer. For this reason it is difficult to prepare copolymers having greater than about 1% of recurring units of vinyl phosphonic acids using conventional methods. By including an alkali metal halide salt, an alkaline earth metal halide salt, or a tetraalkylammonium compound in the aqueous suspension polymerization, the proportion of vinyl phosphonic acid that is chemically incorporated into the polymer can be dramatically increased compared with when the same process run in the absence of the salt or tetraalkylammonium compound.

Vinyl aromatic monomers useful in the processes of the invention include all aromatic ring-containing compounds that have a vinyl or α-substituted vinyl group attached to the aromatic ring. Suitable vinyl aromatic compounds include, but are not limited to, styrene, alkyl-substituted styrenes, α-methylstyrene, alkyl-substituted α-methylstyrenes, tert-butylstyrenes, nuclear methyl styrenes, halogenated styrenes, vinyl naphthalene, and the like, and mixtures thereof. Styrene is the preferred vinyl aromatic monomer.

Vinyl phosphonic acids useful in the processes of the invention have the general structure:

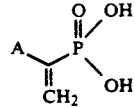

wherein A is selected from the group consisting of hydrogen and $C_1$–$C_{30}$ alkyl, aryl, and aralkyl groups. Preferably, A is selected from the group consisting of hydrogen, methyl, ethyl, propyl, butyl, and phenyl. Examples of suitable vinyl phosphonic acids include, but are not limited to, vinyl phosphonic acid, α-phenylvinyl phosphonic acid, α-methylvinyl phosphonic acid, and the like, and mixtures thereof. α-Phenylvinyl phosphonic acid is preferred.

The radical polymerization catalysts useful in the processes of the invention are any of the peroxide and azo-type initiators well known to those skilled in the art. Generally, the preferred initiators will have a half-life at the reaction temperature greater than about 1 hour. Suitable examples include, but are not limited to, benzoyl peroxide (BPO)-, tert-butyl perbenzoate (TPB), tert-butyl peroxide, azobis(isobutyronitrile), and the like, and mixtures thereof. (Any amount of initiator may be used, although it is preferred to use an amount greater than about 0.05 weight percent based on the weight of monomers used. Preferably, the initiator is benzoyl peroxide, and the polymerization is conducted at about 90° C. Also preferred is the use of tert-butyl perbenzoate either alone or in combination with benzoyl peroxide at polymerization temperatures within the range of about 80° C. to about 150° C.

Partially hydrolyzed polyacrylamide is the only satisfactory suspending agent for suspension copolymerization of vinyl aromatic monomers and vinyl phosphonic acids. Conventional suspending agents such as tricalcium phosphate (TCP), TCP/polyvinyl alcoho (PVA), PVA, barium sulfate, kaolin, and hydroxyethylcellulose generally do not give polymer beads. Partially hydrolyzed polyacrylamide is available from Allied Colloids, Inc., under the tradename "Percol," and from NALCO under the tradename "NALCO-8173." Any effective amount of partially hydrolyzed polyacrylamide can be used. An "effective amount" means, in this context, the amount needed to maintain a stable suspension during the polymerization. Generally, at least about 0.1 weight percent of partially hydrolyzed polyacrylamide based upon the weight of monomers is used.

In one process of the invention, the polymerization of a vinyl aromatic monomer and a vinyl phosphonic acid is performed in the presence of an alkali metal salt or an alkaline earth metal salt. Preferred salts are the alkali metal halides. Any amount of salt can be used, but at least about 5 weight percent based on the amount of water used is needed. Preferably, the amount used is within the range of about 15 to 35 weight percent. This amount is needed to produce copolymers that have greater than about 1 mole percent of vinyl phosphonic acid monomer incorporated into the copolymer. Particularly preferred is a range of about 20 to about 30 weight percent of salt Suitable alkali metal halide salts have the general formula MX, wherein M is a monovalent cation selected from the group consisting of lithium, sodium, and potassium, and X is a halide ion. Examples of suitable alkali metal salts include, but are not limited to, sodium chloride, potassium chloride, lithium bromide, potassium fluoride, sodium iodide, sodium bromide, potassium bromide, and the like, and mixtures thereof. Particularly preferred are sodium chloride, sodium bromide, potassium chloride, and potassium bromide.

Suitable alkaline earth metal halide salts have the general formula $NX_2$, wherein N is a divalent cation selected from the group consisting of calcium and magnesium, and X is a halide ion. Examples of suitable alkaline earth metal halide salts include, but are not limited to, calcium chloride, magnesium bromide, magnesium fluoride, calcium iodide, and the like, and mixtures thereof.

Generally, the amount of salt used and the identity of the salt impact the degree of vinyl phosphonic acid incorporation in the polymer and also affect the bead size. Potassium bromide, for example, gives relatively large beads, while calcium chloride and lithium chloride give small beads. Thus, by selecting the proper salt, one can readily control the approximate size of the resulting polymer beads. By controlling the amount of salt added, one can easily control the proportion of vinyl phosphonate monomer that becomes incorporated into the copolymer. Generally, greater salt concentrations enhance vinyl phosphonate incorporability.

In another embodiment of the invention, a vinyl aromatic monomer and a vinyl phosphonic acid are copolymerized in an aqueous suspension that includes a tetraalkylammonium compound. Partially hydrolyzed polyacrylamide is required as the suspending agent. An advantage of the tetraalkylammonium compounds is that small amounts are effective in producing copolymers with high vinyl phosphonic acid monomer incorporation.

The tetraalkylammonium compounds useful in the process of the invention preferably have the general structure $R_4NX$ wherein each R group separately represents a $C_1$-$C_{24}$ alkyl or aralkyl group, and X is a hydroxide or halide ion. Examples of suitable tetraalkylammonium compounds include, but are not limited to, tetramethylammonium hydroxide, tetra-n-butylammonium hydroxide, n-hexyl-tri-n-butylammonium hydroxide, tetra-pentylammonium hydroxide, tetra-isobutylammonium hydroxide, tetra-n-butylammonium bromide, tetrapentylammonium chloride, tetrahexylammonium chloride, and the like, and mixtures thereof.

Any amount of tetraalkylammonium compound can be used. For reasons of effectiveness and economy, it is preferred to use an amount within the range of about 0.05 to about 1 equivalent of tetraalkylammonium compound per equivalent of vinyl phosphonic acid monomer. A particularly preferred range is about 0.1 to about 0.8 equivalents. Most preferred is the range from about 0.2 to about 0.4 equivalents. When the vinyl phosphonic acid monomer is α-phenylvinyl phosphonic acid, it is preferred to use a tetraalkylammonium compound having $C_4$ to $C_6$ alkyl groups.

The tetraalkylammonium hydroxide compound can be prepared in situ from the reaction of a tetraalkylammonium halide salt and a source of hydroxide ions. For example, tetra-n-butylammonium hydroxide is generated in situ by combining tetra-n-butylammonium bromide and sodium hydroxide. In one process of the invention, for example, about 0.2 equivalents of a mixture of tetra-n-pentylammonium bromide and tetra-n-hexylammonium chloride is combined with from about 0.2 to about 0.25 equivalents of sodium hydroxide per equivalent of vinyl phosphonic acid monomer.

Copolymers of vinyl aromatic monomers and vinyl phosphonic acids made in the presence of tetraalkylammonium compounds contain a proportion of polymer in which a vinyl phosphonic acid proton is replaced by a tetraalkylammonium group.

In another process of the invention, thermoplastic polymer beads are prepared by copolymerizing in an aqueous suspension a vinyl aromatic monomer and a vinyl phosphonate diester. The reaction is performed in the presence of a suspending agent and a radical initiator. In contrast to vinyl phosphonic acids, the suspending agent used for polymerizations with vinyl phosphonate diesters is not especially critical. Any of a variety of well-known suspending agents can be used. Suitable examples include, but are not limited to, partially hydrolyzed polyacrylamide, polyvinyl alcohol, kaolin, tricalcium phosphate, hydroxyethyl cellulose, and the like, and mixtures thereof.

The initiator used to copolymerize vinyl phosphonate diesters is preferably a high-temperature initiator. Suitable high-temperature initiators are compounds that have a half-life of greater than about 1 hour at temperatures greater than about 110° C. Examples of suitable high-temperature initiators include tert-butyl perbenzoate (TPB), 2,5-dimethyl-2,5-bis(2-ethylhexanoylperoxy)hexane, and the like, and mixtures thereof. A low-temperature initiator such as benzoyl peroxide may be used in combination with the high-temperature initiator if desired.

The vinyl phosphonate diesters useful in the process of the invention preferably have the structure:

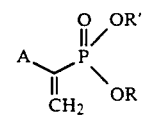

in which A, R, and R' separately represent monovalent radicals selected from the group consisting of hydrogen, $C_1$-$C_{30}$ alkyl, aryl, and aralkyl.

The vinyl phosphonate diesters are alternatively cyclic vinyl phosphonate esters having the structure:

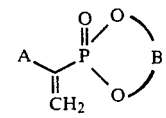

wherein A is as described above, and B is a linear or branched divalent hydrocarbyl radical. Particularly preferred are cyclic diesters in which B is selected from the group consisting of: —CH₂—CH₂— and

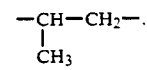

When the process of the invention is performed with vinyl phosphonate diesters, it is preferred to use high-temperature initiators and reaction temperatures greater than about 110° C. Copolymers can be prepared at lower temperatures, but satisfactory beads often cannot be made.

In another process of the invention, thermoplastic polymer beads are prepared by copolymerizing in an aqueous suspension: (a) a vinyl aromatic monomer; and (b) a vinyl phosphonate monoester in the presence of partially hydrolyzed polyacrylamide.

Preferably, the vinyl phosphonate monoester has the structure:

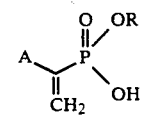

in which A and R separately represent monovalent radicals selected from the group consisting of hydrogen, $C_1$-$C_{30}$ alkyl, aryl, and aralkyl.

The vinyl phosphonate monoester is conveniently prepared by reacting the corresponding diester in aqueous media with at least one equivalent of aqueous base. Preferably, the base is an alkali metal or alkaline earth metal hydroxide, carbonate, bicarbonate, or the like. Acidification of the mixture, preferably with hydrochloric or phosphoric acid, generates the vinyl phosphonate monoester. This aqueous mixture can then be easily combined in any desired manner with a vinyl aromatic monomer, partially hydrolyzed polyacrylamide, and radical initiator to produce copolymers of the vinyl aromatic monomer and the vinyl phosphonate monoester. Alternatively, the vinyl phosphonate monoester can be isolated and purified following preparation from the diester. Usually, it will be more convenient to use the aqueous monoester "as is" for the copolymerization step.

The copolymers of the invention—i.e., copolymers of vinyl aromatic monomers and vinyl phosphonic acids, monoesters, and diesters—are useful for making foamed articles. Thermoplastic expandable copolymer beads are first prepared by aqueous suspension polymerization according to one of the processes described above. The suspension polymerization processes differ depending upon the which type of vinyl phosphonic acid derivative is employed.

The thermoplastic polymer beads may be impregnated with a foaming agent when polymerization is substantially complete. If desired, the foaming agent may be included with the charged reactants so that impregnation of the polymer occurs in situ during the polymerization.

The foaming agents useful in this invention are any of those commonly known to those skilled in the art. Examples include hydrocarbons, such as butanes, pentane, and the like, fluorocarbons, air, carbon dioxide, and other pneumatogens. Any combination of foaming agents may be used. Generally, hydrocarbons are the most suitable foaming agents for in situ impregnations.

It is often desirable to include a wax in the polymerization reaction. Suitable waxes include polyethylene waxes such as "Bareco-1000" wax (Product of Petrolite) and the like. Suitable waxes for use in the invention are soluble in styrene, but relatively insoluble in the polymer product. Useful waxes include, but are not limited to, low molecular weight linear hydrocarbons such as paraffins, natural waxes, Fischer-Tropsch waxes, and the like, and high molecular weight branched hydrocarbons such as high molecular weight polyisobutylene polymers and the like. Mixtures of waxes may be used.

The impregnated beads are thermally expanded to form foamed beads, similar to polystyrene "prepuff." Typically, the expansion is performed by exposing the hard beads to steam. The methods suitable are well known to those skilled in the art.

Suitable molding processes are also well known in the art. Pre-expanded or foamed beads are typically molded under steam pressure until the foamed beads fuse and expand to form a fused, foamed article.

If desired, both a foaming agent and a wax may be included in the polymerization. For example, in one embodiment of the invention, styrene is copolymerized with 1-phenylvinyl phosphonic acid in the presence of pentane and "Bareco-1000" wax. After pre-expansion, the resilient foamed beads are steam molded to give a well-formed part.

Molded articles made by the process of the invention show flame-retardant properties similar to commercial expanded polystyrene containing brominated flame-retardant additives, and can be formulated to pass burn tests such as the UL94HBF test.

The following examples merely illustrate the invention. Those skilled in the art will recognize many possible variations that are within the spirit of the invention and scope of the claims.

EXAMPLES 1-8

Suspension Copolymerization of Styrene and PVPA
Effect of Suspending Agent

A 350-mL pressure bottle was charged with 1-phenylvinyl phosphonic acid (PVPA) (8.5 g, 0.046 mol), styrene (91.5 g, 0.88 mol), deionized water (120 mL), benzoyl peroxide (0.6 g), tert-butyl perbenzoate (0.6 g), suspending agent (see Table 1), and optionally an alkali metal salt (Table 1). The bottle was placed in a temperature-controlled bottle polymerizer and continuously agitated while heating to 90° C over 1 hour. Heating at 90° C. was continued for 6 hours. The temperature was increased to 135° C. over 1 h and maintained at 135° C. for 2 h before cooling to 25° C over a one-hour period. The resulting polymer beads (if they formed) were filtered, washed with water and methanol, and then vacuum dried.

As shown in Table 1, partially hydrolyzed polyacrylamide was the only suspending agent to give polymer beads. If the alkali metal salt was omitted, polymer beads formed (Comparative Example 6), but incorporation of the vinyl phosphonate monomer into the product was minimal.

EXAMPLES 9-14

Suspension Copolymerization of Styrene and PVPA
Effect of other Suspending Agents A 350-mL pressure bottle was charged with PVPA (10 g), styrene (90 g), deionized water (120 mL), benzoyl peroxide (0.6 g), tert-butylperbenzoate (0.6 g), potassium bromide (30 g), and suspending agent (see Table 2). The bottle was placed in a temperature-controlled bottle polymerizer. With continuous agitation, the bottle was heated to 90° C. over 1 hour, and maintained at 90° C. for 6 hours. Temperature was then increased to 135° C. over 1 hour, and kept at 135° C. for 2 hours before cooling to 25° C. over 1 hour. Only partially hydrolyzed polyacrylamide (PAM) was able to hold the suspension to give polymer beads. The results are summarized in Table 2.

EXAMPLES 15-30

Suspension Copolymerization of Styrene and PVPA
Effect of Amount and Identity of Salt on PVPA
Incorporation and Bead Size Distribution The procedure of Examples 1-8 was generally followed. The amount of PVPA charged was 5 mole % based on the total amount of PVPA and styrene used. Partially hydrolyzed polyacrylamide was the only suspending agent used. Benzoyl peroxide was the initiator used for Examples 15-20. "VAZO-67" (2,2'-azobis(2-methylbutyronitrile) (a product of E.I. DuPont de Nemours and Company) was used for Examples 21 and 22. Examples 15-22 were heated only to 90° C. for 6 h, then cooled to 25° C. A combination of benzoyl peroxide and tert-butyl perbenzoate was used for Examples 23-30. The results appear in Table 3.

As Comparative Example 15 illustrates, incorporation of PVPA into the copolymer is low in the absence of an alkali metal or alkaline earth metal salt. Small beads are possible with calcium and lithium salts (Examples 20 and 30), while large beads can be made with NaCl (Example 16), NaBr (Examples 24 and 25), and KBr (Examples 28 and 29).

EXAMPLES 31-45

Suspension Copolymerization of Styrene and PVPA Effect of Tetraalkylammonium Compounds A 350-mL citrate polymerization bottle was charged with styrene (60 g), 1-phenylvinyl phosphonic acid, deionized water (68 g), benzoyl peroxide, tert-butyl perbenzoate, partially hydrolyzed polyacrylamide (0.13 g), tetraalkylammonium compound, and optional base (unstated reactant amounts shown in Table 4). The headspace was purged with nitrogen, and the bottle was capped. The bottle was placed in a temperature-controlled bottle polymerizer and continuously agitated by rocking. The bottle was heated at 90° C. for 12 hours. After cooling to 25° C., the bottle was opened, and the copolymer beads were isolated either by filtration or centrifugation. The beads were washed with deionized water, and then with methanol. The beads were then dried under vacuum (1 mm) at 80° C., and the amount of vinyl phosphonate monomer incorporated into the polymer was measured by determining phosphorus content. The results from a number of runs appear in Table 4.

Comparative Example 31 shows that omission of the tetraalkylammonium compound results in incorporation of only a small percentage (<4 mole %) of the charged phosphonate monomer into the styrene/PVPA copolymer. Examples 32-38 illustrate the process of the invention using tetraalkylammonium halides with or without a base present. Examples 39-43 illustrate the process with tetraalkylammonium hydroxide compounds. Interestingly, 90% phosphonate monomer incorporation was achieved with 13 mole % phenylvinyl phosphonic acid charged. Comparative Examples 44 and 45 illustrate the criticality of using partially hydrolyzed polyacrylamide as the suspending agent. Beads were not obtained with either polyvinyl alcohol or tricalcium phosphate/polyvinyl alcohol.

EXAMPLES 46-58

Suspension Copolymerization of Styrene with PVPA Diesters Effect of Initiator Type A 350-mL polymerization bottle was charged with styrene (104 g), 1-phenylvinyl phosphonic acid dimethyl ester (11 g), deionized water (120 g), initiator(s), and suspending agent(s) (see Table 5). The headspace was purged with nitrogen, and the bottle was capped. The bottle was placed in a temperature-controlled bottle polymerizer and continuously agitated by rocking. The bottle was heated at 90° C. for 6 hours, then at 130° C. for 6 hours. After cooling to 25° C., the bottle was opened, and the copolymer beads were separated from the suspension mixture by filtration or centrifugation. The beads were washed with water, then with methanol, and dried under vacuum (1 mm) at 80° C. The results of several runs with various suspending agents and initiator combinations appear in Table 5.

As shown in Table 5, the choice of suspending agent is not especially critical when a diester of PVPA is used. When benzoyl peroxide was used as the only initiator, the suspension failed (Comparative Examples 52 and 53).

EXAMPLES 59-62

Suspension Copolymerization of Styrene with PVPA Cyclic Diester

A 350-mL citrate polymerization bottle was charged with styrene (60 g), 1-phenylvinyl-1-propylene glycol phosphonate (prepared as in Example 65), deionized water (70 g), benzoyl peroxide (0.20 g), t-butyl perbenzoate (0.15 g) and suspending agent(s) (Table 6). The headspace was purged with nitrogen, and the bottle was capped. The bottle was placed in a temperature-controlled bottle polymerizer and agitated by rocking. The bottle was heated at 90° C. for 6 h, then at 130° C. for 6 h. After cooling to 25° C., the bottle was opened, and the beads were isolated by filtration or centrifugation. The beads were washed with water, then with methanol, and were dried under vacuum (1 mm) at 80° C. Results from several runs appear in Table 6.

The proton-decoupled $^{13}C$ NMR and $^{31}P$ spectra were consistent with a copolymer containing mostly acyclic (ring-opened) propylene glycol ester groups.

COMPARATIVE EXAMPLES 63-64

Bulk Copolymerization of Styrene with PVPA Cyclic Diester

A thick-walled glass tube equipped with a magnetic stir bar was evacuated, flushed with nitrogen, and charged with a premixed solution of styrene (20 g), 1-phenylvinyl-1-propylene glycol phosphonate (prepared as in Example 65), benzoyl peroxide, and t-butyl perbenzoate. The tube was closed and placed in an oil bath. The contents were stirred and heated at 90° C. for 6 h, and at 130° C. for 6 h. The tube was cooled to 30° C., and the copolymer was dissolved in tetrahydrofuran (100 mL). This solution was added to 1500 mL of methanol with stirring. The precipitated solids were washed with methanol and dried under vacuum (1 mm) at 80° C. The results from two runs appear in Table 6.

The proton-decoupled $^{13}C$ NMR and $^{31}P$ spectra were consistent with a copolymer containing only cyclic (ring-intact) propylene glycol ester groups.

EXAMPLE 65

Preparation of Cyclic Propylene Glycol Ester of 1-Phenylvinyl phosphonic acid

A two-liter 3-neck flask equipped with magnetic stirring, addition funnel, thermometer, and inert gas inlet was charged with 1-phenylvinyl phosphonic acid (92 g) and dichloromethane (500 mL), and was cooled to 2° C. Propylene oxide (116 g) was added dropwise over 90 minutes from the addition funnel, during which time the temperature increased to 8° C. The mixture was allowed to warm to 23° C. while stirring for 16 h. Additional dichloromethane (500 mL) was added to the mixture. The organic phase was washed with deionized water (2×200 mL), was dried over magnesium sulfate, and was filtered. Solvent removal by rotary evaporation was followed by distillation at 0.5 mm. The fraction boiling between 160°-165° C. was collected and redistilled at 0.1 mm to give 66 g of 99%-pure 1-phenylvinyl-1-propylene glycol phosphonate. The compound displayed sharp $^{31}P$ NMR signals at 33.2 and 32.9 ppm.

EXAMPLE 66

Preparation of 1-Phenyl-1-Monomethylphosphonate

A 250-mL 3-neck flask equipped with a magnetic stir bar, thermometer, and nitrogen inlet was charged with 1-phenylvinyl-1-dimethylphosphonate (42 g) and deionized water (100 mL) containing dissolved sodium hydroxide (12 g). The reaction mixture was stirred until homogeneous (about 2 h). The reaction mixture was extracted with methyl t-butyl ether (MTBE) (2×100 mL). The aqueous layer was treated with 85% phosphoric acid (39 g) and then extracted with MTBE (4×100 mL). The combined MTBE layers were dried over magnesium sulfate, filtered, and stripped to give the monomethyl phosphonate (33 g, 82%) in adequate purity for polymerization.

EXAMPLE 67

Suspension Copolymerization of Styrene and 1-Phenylvinyl-1-monomethylphosphonate A 350-mL citrate polymerization bottle was charged with styrene (60 g), 1-phenylvinyl-1-monomethylphosphonate (6 g as prepared in the preceding example), deionized water (70 g), benzoyl peroxide (0.20 g), t-butyl perbenzoate (0.15 g), and partially hydrolyzed polyacrylamide (0.13 g). The headspace was purged with nitrogen, and the bottle was capped. The bottle was placed in a temperature-controlled bottle polymerizer and agitated by rocking. The bottle was heated at 90° C. for 6 h, and at 130° C. for 6 h. After cooling to 25° C., the bottle was opened, and the copolymer beads were isolated by filtration or centrifugation. The beads were washed with deionized water, then with methanol, then dried under vacuum (1 mm) at 80° C. Yield: 61 g.

EXAMPLE 68

Suspension Copolymerization of Styrene and 1-Phenylvinyl-1-monomethylphosphonate Prepared In-situ A 350-mL citrate polymerization bottle was charged with 1-phenylvinyl-1-dimethylphosphonate (6.5 g), sodium hydroxide (1.2 g), and deionized water (60 g). After stirring the reaction mixture for 2 h, 37% hydrochloric acid (3.0 g) was added. To this solution was added partially hydrolyzed polyacrylamide (130 mg) and a premixed solution of styrene (60 g), benzoyl peroxide (0.18 g), and t-butyl perbenzoate. The headspace was purged with nitrogen, and the bottle was capped. The bottle was placed in a temperature-controlled bottle polymerizer and was agitated by rocking. The bottle was heated to 90° C. for 6 h and at 130° C. for 6 h. After cooling to 25° C., the bottle was opened and the beads were isolated from the mixture by centrifugation. The beads were washed with deionized water, then with methanol, and dried under vacuum (1 mm) at 80° C. Yield: 62 g. The copolymer contained 1.2 weight percent phosphorus (indicating 88% incorporation of vinylphosphonate monomer).

EXAMPLE 69

Preparation of Foamed Articles from Styrene/PVPA Copolymers Post-polymerization Impregnation A 350-mL pressure bottle was charged with styrene (90 g), 1-phenylvinyl phosphonic acid (PVPA) (10 g), benzoyl peroxide (0.6 g), tert-butyl perbenzoate (0.5 g), deionized water (120 mL), potassium bromide (30 g), partially hydrolyzed polyacrylamide (0.8 g), and, optionally, "Bareco-1000" polyethylene wax (0, 0.2, or 0.4 g) (product of Petrolite). The bottle was agitated in a temperature-controlled polymerizer for 6 h at 90° C. The bottle was heated to 135° C. over 1 h, and kept at 135° C. for 2 h before cooling to 25° C. over 1 h. The resulting polymer beads were filtered, washed successively with water and methanol, and vacuum dried. The mole % PVPA found in the polymer was determined by phosphorus analysis to be 4.0–4.1% (about 67% incorporation of the charged phosphonate monomer).

Copolymer beads prepared as described above were impregnated with pentane as follows. A pressure bottle was charged with polymer beads (55 g), tricalcium phosphate (1.65 g), 1% aqueous dodecylbenzene sulfonate solution ("Naccanol-90G, a product of Stephan Chemical) (0.55 mL), "Tween 20" surfactant (Product of ICI Americas) (0.06–0.6 g), and pentane (4.3–8.6 g). The bottle was agitated at 90° C. for 2 h, and then was heated to 110° C. over 1 h. Heating continued at 110° C. for 2 h before cooling to 25° C. over 6 h. Concentrated hydrochloric acid (10 mL) was added, and the beads were then filtered and washed with distilled water. After air drying for 4 h, the impregnated beads were expanded with steam. The density of the resulting prepuffed beads was within the range of about 1–10 pcf depending on conditions. High-density prepuff beads (greater than about 4 pcf density) were molded into good articles.

EXAMPLE 70

Preparation of Low-Density Beads from Styrene/PVPA Copolymers In-situ Impregnation--No wax The procedure described above was followed with the following modifications: No wax was used. Pentane (7.5–10 g) was included with the initial reactants; thus impregnation was performed during the polymerization. The resulting impregnated beads were air dried for 4 h, then expanded with steam to give low-density (1.5 pcf) prepuffed beads.

EXAMPLE 71

Preparation of a Foamed Article from Styrene/PVPA Copolymer In-situ Impregnation--Polyethylene Wax--KBr A 350-mL pressure bottle was charged with PVPA (10 g, 6 mole %), benzoyl peroxide (0.6 g), tert-butyl perbenzoate (0.5 g), styrene (90 g), deionized water (120 mL), potassium bromide (30 g), "Bareco-1000" polyethylene wax (0.2 g), partially hydrolyzed polyacrylamide (0.8 g), and pentane (10 g). The bottle was agitated at 90° C. for 6 h, and then was heated to 135° C. over 1 h. Heating continued at 135° C. for 2 h before cooling to 25° C. over 1 h. The resulting polymer beads were filtered and washed successively with water and methanol, then air dried for 4 h. The impregnated beads were then expanded with steam at 89° C. for 1 min. to give prepuff. The prepuffed beads were annealled for 16–20 h after steam expansion, then steam molded at 18 psi for 20 s to give a foamed article. (Beads that were expanded at 98° C. for 1–4 minutes gave low-density (<1 pcf) prepuff, but these were not satisfactory for molding.)

EXAMPLES 72–74

Preparation of Foamed Articles from Styrene/PVPA Copolymers In-Situ Impregnation--Polyethylene Wax--Tetraalkylammonium salt A 350-mL pressure bottle was charged with PVPA (5.5 g, 5 mole %), benzoyl peroxide (0.18 g), tert-butyl perbenzoate (0.12 g), styrene (60 g), deionized water (68 mL), tetra-n-butylammonium bromide (2 g), partially hydrolyzed polyacrylamide (0.13 g), n-pentane (4.9 g), and "Bareco-1000" polyethylene wax (see Table 8). The bottle was agitated at 90° C. for 6 h, and then was heated to 135° C. over 1 h. Heating continued at 135° C. for 2 h before cooling to 25° C. over 1 h. The resulting polymer beads were filtered and washed successively with water and methanol, then air dried for 4 h. The impregnated beads were then expanded with steam under the conditions specified in Table 7 to give prepuff. The prepuffed beads were annealled for 16–20 h after steam expansion. Some of the prepuffed beads were steam molded at 20 psi for 15 seconds into foamed articles (Table 7).

EXAMPLE 75

Pentane Impregnation of Poly(styrene-co-1-phenylvinyl-1-dimethylphosphonate), Expansion, and Molding of the same A 350-mL citrate polymerization bottle was charged with 50 g of 14–30 mesh beads of poly(styrene-co-1-phenylvinyl-1-dimethylphosphonate) (prepared as in Example 55), deionized water (50 g), tricalcium phosphate (1.5 g), dodecylbenzene sulfonate (0.5 mL of 1% aqueous solution), "Tween-80" surfactant (Product of ICI Americas) (0.05 g), and pentane (3.9 g). The bottle was capped, placed in a rocker reactor, and with constant agitation, was heated from 25° C. to 90° C. over 1 h, held at 90° C. for 2 h, heated from 90° C. to 120° C. over 1 h, held at 120° C. for 2 h, and cooled to 25° C. over 6 h. The bottle was opened, and 12N HCl (25 mL) was added with shaking. The beads were isolated by centrifugation and rinsed with deionized water. The beads were dried by centrifugation, and air dried 3 h. After air drying, a portion of the beads was analyzed for volatile content by weighing, heating in an oven at 150° C. for 1 h, and reweighing. Volatile content of the beads was about 6%.

Beads as prepared above were expanded by steaming at 100° C. for 30 s. The expanded beads were allowed to cure overnight. The dried beads had a density of about 1 pcf. The cured beads were molded into foam parts by vacuuming the expanded beads into a preheated (130° C.) mold of the desired shape. Foam parts of poly(styrene-co-1-phenylvinyl-1-dimethylphosphonate) containing 5 mole percent of the phosphonate diester recurring units (1.3 weight percent phosphorus content) passed the UL94HBF test.

EXAMPLE 76

Preparation, In-situ Impregnation, Expansion, and Molding of Poly(styrene-co-1-phenylvinyl-1-propylene glycol phosphonic acid)

A 350-mL citrate polymerization bottle was charged with styrene (60 g, 0.58 mol), 1-phenylvinyl-1-propylene glycol phosphonate (prepared as in Example 65) (7.0 g, 0.31 mol), deionized water (70 g), benzoyl peroxide (0.20 g), tert-butyl perbenzoate (0.12 g), partially hydrolyzed polyacrylamide (0.27 g), "Bareco-1000" wax (0.20 g), and pentane (3.5 g). The headspace was purged with nitrogen, and the bottle was capped. The bottle was placed in a temperature-controlled bottle polymerizer, and was agitated by rocking. The bottle was heated at 90° C. for 6 h, and at 130° C. for 6 h. After cooling to 25° C., the bottle was opened and the beads were isolated by filtration. The beads were allowed to air dry for 16 h, and were then expanded with steam at 98° C. for 90 s to give prepuff beads with a density of 1.4 pcf. After a 16-h annealling period, the prepuff was molded into a well-fused part.

TABLE 1

Suspension Copolymerization of Styrene and PVPA Effect of Suspending Agent

| | Suspending Agent | | | | | Polymer |
|---|---|---|---|---|---|---|
| Ex | TCP (g) | PVA (g) | PAM (g) | Salt | Wt %* | beads? |
| C1 | 0.75 | 2.25 | 0 | — | 0 | No |
| C2 | 0.75 | 0 | 0 | NaCl | 20 | No |
| C3 | 0.75 | 2.25 | 0 | NaCl | 20 | No |
| C4 | 0.75 | 2.25 | 0 | NaBr | 20 | No |
| C5 | 0.75 | 5.0 | 0 | KBr | 25 | No |
| C6 | 0 | 0 | 0.4 | — | 0 | Yes |
| 7 | 0 | 0 | 0.4 | NaCl | 20 | Yes |
| 8 | 0 | 0 | 0.4 | KBr | 25 | Yes |

TCP = tricalcium phosphate; PVA = polyvinyl alcohol (1 wt. % aqueous solution); PAM = partially hydrolyzed polyacrylamide.
Benzoyl peroxide (0.6 g) and tert-butyl perbenzoate (0.6 g) were used as initiators for each run.
*Weight percent of salt used based on the amount of water present.

TABLE 2

Suspension Copolymerization of Styrene and PVPA Effect of Other Suspending Agents

| Ex | Suspending agent | Amount (g) | Suspension results |
|---|---|---|---|
| 9 | PAM | 0.4 | Beads |
| C10 | HyEtCell/PVA | 0.6/0.6 | Failed |
| C11 | Xanthan Gum | 0.12 | Failed |
| C12 | PAA | 1.2 | Failed |
| C13 | TAMOL/HyEtCell | 1.2/0.6 | Failed |
| C14 | barium sulfate | 0.92 | Failed |

PAM = Partially hydrolyzed polyacrylamide;
HyEtCell = hydroxyethyl cellulose;
PAA = sodium salt of polyacrylic acid (MW = 6000);
TAMOL (A product of Rohm and Haas Company) = sodium salt of condensed naphthalenesulfonic acid

TABLE 3

Suspension Copolymerization of Styrene and PVPA using Partially Hydrolyzed Polyacrylamide
Effect of Salt on Vinyl Phosphonic Acid Monomer Incorporation and on Bead-Size Distribution

| | | | | | Bead Size Distribution (%) | | |
|---|---|---|---|---|---|---|---|
| Ex | Salt | Wt % | Initiator | Mole % PVA | <16 m | 16–45 m | >45 m |
| C15 | — | 0 | A | 0.4 | 0 | 90 | 10 |
| 16 | NaCl | 10 | A | 3.5 | 69 | 29 | 2 |
| 17 | NaCl | 20 | A | 4.5 | 35 | 61 | 4 |
| 18 | NaCl | 25 | A | — | suspension failed | | |
| 19 | CaCl$_2$ | 10 | A | 2.0 | 36 | 62 | 2 |

TABLE 3-continued

Suspension Copolymerization of Styrene and PVPA
using Partially Hydrolyzed Polyacrylamide
Effect of Salt on Vinyl Phosphonic Acid Monomer
Incorporation and on Bead-Size Distribution

| Ex | Salt | Wt % | Initiator | Mole % PVA | Bead Size Distribution (%) <16 m | 16–45 m | >45 m |
|---|---|---|---|---|---|---|---|
| 20 | $CaCl_2$ | 20 | A | 4.9 | 0.4 | 43 | 56 |
| 21 | NaCl | 10 | B | 3.8 | 56 | 43 | 1 |
| 22 | NaCl | 20 | B | — | suspension failed | | |
| 23 | NaCl | 20 | C | 4.5 | 0 | 81 | 19 |
| 24 | NaBr | 20 | C | 3.1 | 87 | 12 | 1 |
| 25 | NaBr | 25 | C | 3.8 | 88 | 11 | 0.4 |
| 26 | NaBr | 30 | C | 3.8 | 44 | 55 | 1 |
| 27 | KBr | 20 | C | 2.4 | 23 | 73 | 4 |
| 28 | KBr | 25 | C | 3.6 | 95 | 5 | 0 |
| 29 | KBr | 30 | C | 4.2 | 98 | 2 | 0 |
| 30 | LiCl | 20 | C | 4.2 | 4 | 44 | 52 |

Initiators: A—benzoyl peroxide (0.6 g); B—VAZO-67 (0.6 g); C—benzoyl peroxide (0.6 g) and tert-butyl perbenzoate (0.6 g).
Mole % PVPA is the mole percent of 1-phenylvinyl phosphonic acid incorporated into the polymer calculated from P elemental analysis (5 mole % = quantitative).
Bead sizes are mesh values—distributions are in weight percent.

TABLE 4

Suspension Copolymerization of Styrene and PVPA
Effect of Tetraalkylammonium Compounds

| Ex # | Mol % PVPA charged | Suspend Agent | $R_4N+$ Cpd. | Eq. | Base Cpd. | Eq. | Mol % PVPA in copolymer | % PVPA incorp. | Beads form? |
|---|---|---|---|---|---|---|---|---|---|
| C31 | 5 | PAM | — | — | — | — | 0.17 | 3.4 | Yes |
| 32 | 5 | PAM | TBAB | 0.30 | — | — | 3.8 | 76 | Yes |
| 33 | 5 | PAM | TBAB | 0.20 | NaOH | 0.22 | 3.5 | 70 | Yes |
| 34 | 5 | PAM | THXAC | 0.20 | — | — | 4.2 | 84 | Yes |
| 35 | 5 | PAM | TPNAB | 0.28 | — | — | 4.2 | 84 | Yes |
| 36 | 5 | PAM | TPNAB | 0.28 | NaOH | 0.22 | 3.8 | 76 | Yes |
| 37 | 5 | PAM | TPNAB | 0.28 | $Na_2CO_3$ | 0.22 | 3.8 | 76 | Yes |
| 38 | 5 | PAM | TPNAB | 0.28 | $NaHCO_3$ | 0.20 | 4.2 | 84 | Yes |
| 39 | 5 | PAM | TBAH | 0.10 | — | — | 3.1 | 62 | Yes |
| 40 | 5 | PAM | TBAH | 0.20 | — | — | 3.5 | 70 | Yes |
| 41 | 7 | PAM | TBAH | 0.20 | — | — | 4.9 | 70 | Yes |
| 42 | 13 | PAM | TBAH | 0.21 | — | — | 11.7 | 90 | Yes |
| 43 | 5 | PAM | BTMAH | 0.05 | — | — | 1.4 | 28 | Yes |
| C44 | 5 | PVA | TBAH | 0.20 | — | — | — | — | No |
| C45 | 5 | PVA/TCP | TBAH | 0.20 | — | — | — | — | No |

Mol % PVPA charged = mole percent of 1-phenylvinyl phosphonic acid charged relative to total monomer.
Initiator = benzoyl peroxide(BPO)/t-butyl perbenzoate(TPB) (0.3/0.2 wt % based on styrene) in each example except Ex 41 (BPO/TPB = 0.5/0.3 wt %) and Ex 43 (BPO = 0.3 wt %).
Suspending agents: PAM = partially hydrolyzed polyacrylamide; PVA = polyvinyl alcohol; TCP = tricalcium phosphate.
Tetraalkylammonium compounds: TBAB = tetra-n-butylammonium bromide; THXAC = tetra-n-hexylammonium chloride; TPNAB = tetra-n-pentylammonium bromide; TBAH = tetra-n-butylammonium hydroxide; BTMAH = benzyltrimethylammonium hydroxide.
Mol % PVPA in copolymer calculated from phosphorus elemental analysis.
% PVPA incorp = percentage of charged 1-phenylvinyl phophonic acid that was incorporated into the copolymer.

TABLE 5

Suspension Copolymerization of Styrene and PVPA Diesters
Effect of Suspending Agent and Initiator

| Ex | Suspend Agent (wt %) PAM | TCP | PVA | Initiator (wt %) BPO | TPB | Mole % dimethyl ester charged | Mole % dimethyl ester in Copolymer |
|---|---|---|---|---|---|---|---|
| 46 | 0 | 2.5 | 7.5 | 0.2 | 0.1 | 1.0 | 0.95 |
| 47 | 0.2 | 0 | 0 | 0.2 | 0.1 | 1.0 | 0.78 |
| 48 | 0 | 0.8 | 2.4 | 0.3 | 0.15 | 2.0 | 1.6 |
| 49 | 0.4 | 0 | 0 | 0.3 | 0.15 | 2.0 | 1.9 |
| 50 | 0.4 | 0 | 0 | 0.3 | 0.15 | 3.0 | 2.2 |
| 51 | 0.4 | 0 | 0 | 0.3 | 0.15 | 4.0 | 3.2 |
| C52 | 0.4 | 0 | 0 | 0.3 | 0 | 5.0 | No Beads |
| C53 | 0 | 0.7 | 0 | 0.3 | 0 | 5.0 | No Beads |
| 54 | 0.4 | 0 | 0 | 0.3 | 0.15 | 5.0 | 4.2 |
| 55 | 0 | 0.7 | 2.3 | 0.3 | 0.15 | 5.0 | 4.6 |
| 56 | 0.4 | 0 | 0 | 0.3 | 0.15 | 9.0 | 10.4 |
| 57 | 0 | 0.7 | 2.3 | Note A | | 5.0 | 4.2 |

TABLE 5-continued

Suspension Copolymerization of Styrene and PVPA Diesters
Effect of Suspending Agent and Initiator

| Ex | Suspend Agent (wt %) PAM | TCP | PVA | Initiator (wt %) BPO | TPB | Mole % dimethyl ester charged | Mole % dimethyl ester in Copolymer |
|---|---|---|---|---|---|---|---|
| 58 | 0.2 | 0 | 0 | Note B | | 5.0 | 4.2 |

PAM = partially hydrolyzed polyacrylamide; TCP = tricalcium phosphate;
PVA = polyvinylalcohol (1 wt. % aqueous solution); BPO = benzoyl peroxide; TPB = tert-butyl perbenzoate.
Note A: "Lupersol 256" initiator (product of Pennwalt) (0.55 g) was used; reaction at 90° C. for 5 h, then at 120° C. for 5 h.
Note B: "VAZO 88" initiator (product of DuPont) (0.25 g) and TPS (0.14 g) were used as the initiators.
Mole % dimethyl ester in copolymer calculated from phosphorus elemental analysis.

TABLE 6

Copolymerization of Styrene and Cyclic Vinylphosphonate Ester

| Ex # | Polym. type | Init Wt % BPO/TPB | Suspend Wt % PAM/TCP/PVA | Mole % PVPGP charged | Mole % PVPGP in Copolymer | Beads form? |
|---|---|---|---|---|---|---|
| 59 | Suspen. | 0.3/0.2 | 0.4/0/0 | 1 | 0.51 | Yes |
| 60 | Suspen. | 0.3/0.2 | 0.4/0/0 | 5 | 3.9 | Yes |
| 61 | Suspen. | 0.3/0.2 | 0.4/0/0 | 10 | 10.6 | Yes |
| C62 | Suspen. | 0.3/0.2 | 0/0.8/2.3 | 5 | — | No |
| C63 | Bulk | 0.3/0.2 | — | 5 | 5.0 | — |
| C64 | Bulk | 0.3/0.2 | — | 10 | 10.6 | — |

BPO = benzoyl peroxide; TPB = tert-butyl perbenzoate
PAM = partially hydrolyzed polyacrylamide; TCP = tricalcium phosphate;
PVA = polyvinyl alcohol (1 wt. % aqueous solution).
Mole % PVPGP charged - mole % of 1-phenylvinyl-1-propylene glycol phosphonate charged relative to total monomer.
Mole % PVPGP in copolymer is the calculated amount from phosphorus elemental analysis.

TABLE 7

PVPA/Styrene Copolymers made w/ In-situ Impregnation
Wax--Bu4NBr (Examples 72-74)
Prepuff densities and molding results

| Ex # | | Wax[1] (wt %) | Prepuff conditions Temp (°C.) | Time (min) | Prepuff density (pcf) | Sample molded?[2] |
|---|---|---|---|---|---|---|
| 72 | a | 0.10 | 98 | 1.0 | 1.1 | No |
|  | b |  | 92 | 1.0 | 2.0 | No |
|  | c |  | 90 | 1.0 | 2.0 | No |
| 73 | a | 0.20 | 98 | 1.0 | 1.2 | No |
|  | b |  | 95 | 1.0 | 1.1 | Yes |
|  | c |  | 92 | 1.0 | 1.4 | Yes |
|  | d |  | 90 | 1.0 | 1.7 | Yes |
| 74 | a | 0.40 | 98 | 1.0 | 1.1 | No |
|  | b |  | 92 | 1.0 | 2.1 | No |

[1]Weight % of "BARECO-1000" wax based on total monomer.
[2]Low-density beads that were pre-expanded at 90-95° C. were molded into well-formed articles; molding of higher density beads and beads pre-expanded at 98° C. was not attempted.

We claim:

1. A process for making a foamed article, said process comprising molding foamed beads prepared by thermally expanding thermoplastic polymer beads, said thermoplastic polymer beads made by copolymerizing in an aqueous suspension a vinyl aromatic monomer and a vinyl phosphonic acid derivative selected from vinyl phosphonic acids and vinyl phosphonate mono- and diesters.

2. The process of claim 1 wherein the copolymerization is performed in the presence of a foaming agent, and impregnation of the polymer beads occurs in situ as the monomers polymerize.

3. The process of claim 2 wherein the foaming agent is one or more agents selected from the group consisting of butanes, and pentanes, and fluorocarbons.

4. The process of claim 1 wherein a foaming agent is added to the polymer beads when the copolymerization is substantially complete.

5. The process of claim 4 wherein the foaming agent is one or more agents selected from the group consisting of butanes, pentanes, fluorocarbons, air, and carbon dioxide.

6. The process of claim 1 wherein the copolymerization is performed in the presence of a wax.

7. A process for making expandable thermoplastic polymer beads, said process comprising:
copolymerizing in an aqueous suspension:
(a) a vinyl aromatic monomer; and
(b) a vinyl phosphonic acid;
in the presence of one or more radical polymerization catalysts, an effective amount of partially hydrolyzed polyacrylamide, and at least about 5 weight percent of an alkali metal halide or alkaline earth metal halide salt based on the amount of water used, to form expandable thermoplastic polymer beads.

8. The process of claim 7 wherein the vinyl aromatic monomer is one or more compounds selected from the group consisting of styrene, nuclear methyl styrenes, halogenated styrenes, alkyl-substituted styrenes, α-methylstyrene, and tert-butylstyrenes.

9. The process of claim 7 wherein the vinyl aromatic monomer is styrene, and the vinyl phosphonic acid is 1-phenyl vinyl phosphonic acid.

10. The process of claim 7 wherein the vinyl phosphonic acid has the structure:

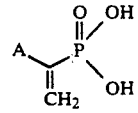

in which A is selected from the group consisting of hydrogen, $C_1$-$C_{30}$ alkyl, aryl, and aralkyl.

11. The process of claim 7 wherein the alkali metal halide salt has the formula MX wherein M is a monovalent cation selected from the group consisting of lithium, sodium, and potassium, and X is a halide ion.

12. The process of claim 7 wherein the alkaline earth metal halide salt has the formula NX$_2$ wherein N is a divalent cation selected from the group consisting of calcium and magnesium, and X is a halide ion.

13. A process for making expandable thermoplastic polymer beads, said process comprising:
  copolymerizing in an aqueous suspension:
  (a) a vinyl aromatic monomer; and
  (b) a vinyl phosphonic acid;
  in the presence of one or more radical polymerization catalysts, an effective amount of partially hydrolyzed polyacrylamide, and a tetraalkylammonium compound to form expandable thermoplastic polymer beads.

14. The process of claim 13 wherein the vinyl aromatic monomer is one or more compounds selected from the group consisting of styrene, nuclear methyl styrenes, halogenated styrenes, alkyl-substituted styrenes, α-methylstyrene, and tert-butylstyrenes.

15. The process of claim 13 wherein the vinyl aromatic monomer is styrene, and the vinyl phosphonic acid is 1-phenyl vinyl phosphonic acid.

16. The process of claim 13 wherein the vinyl phosphonic acid has the structure:

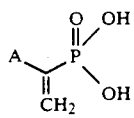

in which A is selected from the group consisting of hydrogen, C$_1$-C$_{30}$ alkyl, aryl, and aralkyl.

17. The process of claim 13 wherein the amount of tetralkylammonium compound is within the range of about 0.05 to about 0.8 equivalents per mole of vinyl phosphonic acid.

18. The process of claim 13 wherein the tetraalkylammonium compound is one or more compounds of the formula R$_4$NX wherein each R group separately represents a C$_1$-C$_{24}$ alkyl or aralkyl group, and X is a halide or hydroxide ion.

19. A process for making expandable thermoplastic polymer beads, said process comprising:
  copolymerizing in an aqueous suspension:
  (a) a vinyl aromatic monomer; and
  (b) a vinyl phosphonate diester in the presence of a suspending agent and a high-temperature radical initiator to form expandable thermoplastic polymer beads.

20. The process of claim 19 wherein the radical initiator has a half-life greater than about one hour at 110° C.

21. The process of claim 19 wherein the vinyl aromatic monomer is one or more compounds selected from the group consisting of styrene, nuclear methyl styrenes, halogenated styrenes, alkyl-substituted styrenes, α-methylstyrene, and tert-butylstyrenes.

22. The process of claim 19 wherein the vinyl aromatic monomer is styrene, and the vinyl phosphonate diester is a dialkyl ester of 1-phenyl vinyl phosphonic acid.

23. The process of claim 19 wherein the vinyl phosphonate diester has the structure:

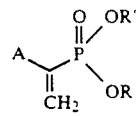

in which A, R, and R' separately represent monovalent radicals selected from the group consisting of hydrogen, C$_1$-C$_{30}$ alkyl, aryl, and aralkyl.

24. The process of claim 19 wherein the vinyl phosphonate diester has the structure:

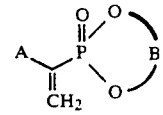

wherein A is a monovalent radical selected from the group consisting of hydrogen, C$_1$-C$_{30}$ alkyl, aryl, and aralkyl; and B is a linear or branched divalent hydrocarbyl radical.

25. The process of claim 24 wherein B is selected from the group consisting of —CH$_2$—CH$_2$—and

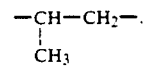

26. A process for making expandable thermoplastic polymer beads, said process comprising:
  copolymerizing in an aqueous suspension:
  (a) a vinyl aromatic monomer; and
  (b) a vinyl phosphonate monoester in the presence of one or more radical polymerization catalysts and partially hydrolyzed polyacrylamide to form expandable thermoplastic polymer beads.

27. The process of claim 26 wherein the vinyl aromatic monomer is one or more compounds selected from the group consisting of styrene, nuclear methyl styrenes, halogenated styrenes, alkyl-substituted styrenes, α-methylstyrene, and tert-butylstryrenes.

28. The process of claim 26 wherein the vinyl aromatic monomer is styrene, and the vinyl phosphonate monoester is a monoalkyl ester of 1-phenyl vinyl phosphonic acid.

29. The process of claim 26 wherein the vinyl phosphonate monoester has the structure:

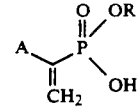

in which A and R separately represent monovalent radicals selected from the group consisting of hydrogen, C$_1$-C$_{30}$ alkyl, aryl, and aralkyl.

30. The process of claim 26 wherein the aqueous suspension contains crude aqueous vinyl phosphonate monoester obtained as the reaction product from basic hydrolysis and acidification of the corresponding vinyl phosphonate diester.

* * * * *